United States Patent
Mendrok-Edinger et al.

(10) Patent No.: US 11,191,772 B2
(45) Date of Patent: *Dec. 7, 2021

(54) USE

(71) Applicant: DSM IP ASSETS B.V., Heerlen (NL)

(72) Inventors: Christine Mendrok-Edinger, Kaiseraugst (CH); Sebastien Mongiat, Kaiseraugst (CH); Thomas Rudolph, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/628,797

(22) PCT Filed: Jun. 28, 2018

(86) PCT No.: PCT/EP2018/067368
§ 371 (c)(1),
(2) Date: Jan. 6, 2020

(87) PCT Pub. No.: WO2019/007790
PCT Pub. Date: Jan. 10, 2019

(65) Prior Publication Data
US 2020/0138841 A1 May 7, 2020

(30) Foreign Application Priority Data
Jul. 6, 2017 (EP) .................... 17180056

(51) Int. Cl.
| | | |
|---|---|---|
| A61K 31/7004 | (2006.01) | |
| A61K 8/06 | (2006.01) | |
| A61K 8/60 | (2006.01) | |
| A61Q 5/00 | (2006.01) | |
| A61Q 5/12 | (2006.01) | |
| A61Q 15/00 | (2006.01) | |
| A61Q 17/00 | (2006.01) | |
| A61Q 19/10 | (2006.01) | |

(52) U.S. Cl.
CPC .......... *A61K 31/7004* (2013.01); *A61K 8/062* (2013.01); *A61K 8/064* (2013.01); *A61K 8/60* (2013.01); *A61Q 5/006* (2013.01); *A61Q 5/12* (2013.01); *A61Q 15/00* (2013.01); *A61Q 17/005* (2013.01); *A61Q 19/10* (2013.01)

(58) Field of Classification Search
CPC ..... A61K 31/7004; A61K 8/062; A61K 8/064
See application file for complete search history.

(56) References Cited

U.S. PATENT DOCUMENTS

| | | | |
|---|---|---|---|
| 6,113,888 A | 9/2000 | Castro et al. | |
| 8,747,818 B1 | 6/2014 | Gross | |
| 10,933,002 B2 * | 3/2021 | Mendrok-Edinger | ....................... A61K 8/042 |
| 2007/0122364 A1 | 5/2007 | Kelly et al. | |
| 2009/0208430 A1 | 8/2009 | Polonka et al. | |
| 2013/0315849 A1 | 11/2013 | Farwick et al. | |

FOREIGN PATENT DOCUMENTS

| | | |
|---|---|---|
| EP | 0 221 728 | 5/1987 |
| WO | 2005/004833 | 1/2005 |

OTHER PUBLICATIONS

International Search Report for PCT/EP2018/067368, dated Sep. 11, 2018, 4 pages.
Written Opinion of the ISA for PCT/EP2018/067368, dated Sep. 11, 2018, 6 pages.
Elseviers et al., "A sweet tooth? dental plaque and the use of anti-cariogenic sweeteners", Agro-Industri Hi-Tech, Teknoscience, Jan. 1, 2000, pp. 24-29.

* cited by examiner

*Primary Examiner* — Pancham Bakshi
(74) *Attorney, Agent, or Firm* — Nixon & Vanderhye P.C.

(57) ABSTRACT

The present invention relates to the use of erythrulose as antimicrobial agent as well as to composition comprising said agent.

11 Claims, No Drawings

USE

This application is the U.S. national phase of International Application No. PCT/EP2018/067368 filed 28 Jun. 2018, which designated the U.S. and claims priority to EP Patent Application No. 17180056.8 filed 6 Jul. 2017, the entire contents of each of which are hereby incorporated by reference.

The present invention relates to the use of erythrulose as antimicrobial agent as well as to composition comprising said agent.

To protect cosmetic compositions, household products, plastics, paper and/or paints against mold and bacteria, most products currently on the market contain preservatives. While these preservatives protect against bacteria and fungi, studies have linked daily exposure to many of these substances to an increased risk of skin irritation, cancer and/or endocrine problems. Thus, many manufactures are searching for alternative antimicrobial actives which allow reducing the amount of preservatives and don't appear to pose any health risks.

Antimicrobial active compounds furthermore play a key role for many cosmetic applications:

Acne is taken to mean a skin disorder which is evident in inflamed papules, pustules or nodules, caused by increased talc production and impaired keratinization of the skin. The inflammation may be associated with reddening, swelling and pressure pain. Besides genetic predisposition, possible causes of acne formation can be androgens, comedogenic substances (for example in cosmetics), smoking, stress or excessive colonization of the skin by bacteria. Acne can be triggered, for example, by microorganisms, such as *Propionibacterium acnes*, or *Staphylococcus epidermidis*. *Propionibacterium acnes* is a bacterium which usually colonizes the skin and lives on sebum. Acne may arise, for example, if the number of these bacteria is increased. The presence of bacteria in the follicles results in inflammation reactions, which is evident in the form of red nodules or pustules. The production of free fatty acids by the bacteria furthermore promotes the inflammation reaction in the follicle.

Besides water and salt, axillary sweat contains many other substances (such as fats, amino acids, sugars, lactic acid, urea, etc.). Freshly formed sweat is odorless; the typical sweat odor only forms due to the action of skin bacteria on the sweat, which decompose the latter. Examples of such bacteria are *Staphylococcus* or *Corynebacterium*. For this reason, antimicrobial substances are usually also employed besides aroma substances and antiperspirants in deodorants, with the aim of controlling the bacteria which are involved in the odor formation.

Surprisingly, it has now been found that erythrulose excerpts a particularly pronounced anti-microbial activity against certain microbes such as in particular *Propionibacterium acnes, Staphylococcus epidermis, Cornyebacterium xerosis*, and/or *Aspergillus brasiliensis*.

Thus, the present invention relates to the use of erythrulose as antimicrobial agent, i.e. an agent which exhibits an antimicrobial activity. In particular the present invention is directed to the use of erythrulose as anti-fungal and/or anti-bacterial agent, more in particular as an agent for killing and/or inhibiting the growth of *Propionibacterium acnes* (*P. acnes*), *Staphylococcus epidermis* (*S. epidermis*), *Cornyebacterium xerosis* (*C. xerosis*), *Aspergillus brasiliensis* (*A. brasiliensis*), *Candida albicans* (*C. albicans*), *Pseudomonas aeruginosa* (*P. aeruginosa*), *Escherichia coli* (*E. coli*) and/or *Staphylococcus aureus* (*S. aureus*), such as most in particular *Propionibacterium acnes, Staphylococcus epidermis, Cornyebacterium xerosis*, and/or *Aspergillus brasiliensis*.

In another embodiment, the invention relates to a method for killing and/or inhibiting growth of microbial cells, in particular fungal and/or bacterial cells, said method comprising contacting said microbial cells with erythrulose. In a preferred embodiment the microbial cells are selected from the group consisting of *Propionibacterium acnes* (*P. acnes*), *Staphylococcus epidermis* (*S. epidermis*), *Cornyebacterium xerosis* (*C. xerosis*), *Aspergillus brasiliensis* (*A. brasiliensis*), *Candida albicans* (*C. albicans*), *Pseudomonas aeruginosa* (*P. aeruginosa*), *Escherichia coli* (*E. coli*) and/or *Staphylococcus aureus* (*S. aureus*) as well as mixtures thereof. Preferably, in all embodiments of the present invention erythrulose is used as agent against *Propionibacterium acnes, Staphylococcus epidermis, Cornyebacterium xerosis*, and/or *Aspergillus brasiliensis*.

In all embodiments of the present invention erythrulose is preferably used for killing and/or inhibiting the growth of *Staphylococcus epidermis* and/or *Cornyebacterium xerosis* as it is particularly efficient against these microbes, which makes it particularly suitable for deodorant applications.

The term "erythrulose" refers to erythrulose in D- or L-form or as the racemate. Preferably L-(+)-Erythrulose [533-50-6] is used. Erythrulose is e.g. commercially available at DSM Nutritional Products Ltd, Kaiseraugst.

The term "antimicrobial activity" (or "antimicrobial effect") as used herein means a capability of killing and/or inhibiting the growth of microbial cells such as in particular bacteria and fungi and more in particular *P. acnes, S. epidermis, C. xerosis, A. brasiliensis, C. albicans, P. aeruginosa, E. coli* and/or *S. aureus*.

Due to the antimicrobial activity, erythrulose is also suitable to maintain skin homeostasis and/or balance the skin microbiome by treating overpopulation of microorganisms on the skin such as *P. acnes* (acne control application) and *S. epidermis* and *C. xerosis* (antiperspirant/deodorant applications) and/or reducing unwanted microorganisms such as *S. aureus*.

In all embodiments of the present invention erythrulose as an antimicrobial agent is preferably used in an amount selected in the range of about 0.005 to 0.75 wt.-%, more preferably in the range of about 0.01 to 0.6 wt.-% and most preferably in the range of 0.025 to 0.5 wt.-% such as in the range of 0.04 to 0.5 wt.-%, based on the total weight of the composition. Further particular suitable ranges include 0.01 to 0.2 wt.-% or 0.05 to 0.2 wt.-%, in particular for the selective treatment of *P. acnes*, A. *Brasiliensis, S. epidermis* and/or *C. xerosis*.

To make use of the anti-microbial activity of erythrulose, it can be used in a multiplicity of formulations or applications, such as, for example, cosmetic or pharmaceutical compositions, medicinal products, household products, plastics, plastisols, paper and/or paints.

In particular the present invention relates to the use of erythrulose for improving preservation, in particular of a product selected from the group of cosmetic compositions, household products, plastics, paper and/or paints compared to the product not containing erythrulose and optionally appreciating the effect, preferably in view of *Aspergillus brasiliensis*.

Thus, in another embodiment, the invention relates to a method of preventing microbial decay and breakdown in particular caused by molds such as most in particular by *Aspergillus brasiliensis*, of cosmetic and/or pharmaceutical compositions, household products, plastics, paper and/or paints, wherein said method comprises adding to the compositions, products, plastics, papers and/or paints erythrulose in an amount of 0.005 to 0.75 wt.-%, more preferably in the range of about 0.01 to 0.6 wt.-%, most preferably in the range of about 0.025 to 0.5 wt.-% such as in the range of 0.04 to 0.5 wt.-% as an antimicrobial agent. Further particular ranges include 0.01 to 0.2 wt.-% or 0.05 to 0.2 wt.-%, respectively 0.01 to 0.15 or 0.05 to 0.15 wt.-% as erythrulose is particularly active against *A. brasiliensis* in such low amounts. In a particular embodiment, the method also encompasses the step of appreciating the result.

In a particular advantageous embodiment, the invention relates to a method of preventing microbial decay and breakdown of cosmetic or pharmaceutical compositions, in particular caused by molds such as most in particular by *Aspergillus brasiliensis*, which compositions furthermore comprise water and at least one further agent selected from the group consisting of surfactants, emulsifiers, thickeners, and oils as such compositions are particular sensitive to microbial growth.

Thus, in another embodiment, the invention is also directed to cosmetic or pharmaceutical compositions comprising water and at least one agent selected from the group consisting of surfactants, emulsifiers, thickeners and oils, wherein the composition furthermore comprises erythrulose in an amount of 0.005 to 0.75 wt.-%, more preferably in the range of about 0.01 to 0.6 wt.-%, most preferably in the range of about 0.025 to 0.5 wt.-% such as in the range of 0.04 to 0.5 wt.-%, and most preferably in the range of 0.04 to 0.2 wt.-%, e.g. in the range of 0.05 to 0.1 wt.-%, based on the total weight of the composition. Further particular ranges include 0.01 to 0.2 wt.-% or 0.05 to 0.2 wt.-%, respectively 0.01 to 0.15 or 0.05 to 0.15 wt.-%.

The present invention furthermore relates to the use of erythrulose as anti-acne, deodorant or antiperspirant active compound. In particular, erythrulose is suitable for the treatment or prophylaxis of acne which is triggered by *P. Acnes* or *S. epidermidis*.

Thus, in another advantageous embodiment the cosmetic or pharmaceutical compositions according to the present invention are anti-acne compositions comprising erythrulose in an amount of 0.01 to 0.15 wt.-%, preferably in the range of 0.05 to 0.15 wt.-%, based on the total weight of the composition as these compositions are particularly suitable treat acne caused by *S. epidermis* and/or *P. acnes* by killing respectively significantly inhibiting the growth of these specific bacteria selectively at this concentration range.

Also advantageous is the use of erythrulose as active compound in deodorants or antiperspirants as it has an antimicrobial action against the bacteria which are responsible for the decomposition of sweat and thus for the formation of the odour, i.e. *S. epidermis* and *C. xerosis* as erythrulose is particularly active against the bacteria responsible for the unwanted odor formation, even at very low concentrations of less than 0.15 wt.-%.

Thus, in another advantageous embodiment the cosmetic or pharmaceutical compositions according to the present invention are deodorant compositions comprising erythrulose in an amount of 0.01 to 0.15 wt.-%, preferably in the range of 0.05 to 0.15 wt.-%, based on the total weight of the composition as these compositions are particularly suitable to avoid the unpleasant odor formation caused by *S. epidermis* and/or *C. xerosis* by killing respectively significantly inhibiting the growth of these specific bacteria selectively at this concentration range.

Advantageously, erythrulose can also be used in combination with traditional preservatives to improve the preservative activity thereof.

The use according to the invention of erythrulose can take place both in the cosmetic sense and also in the pharmaceutical sense. A pharmaceutical application is conceivable, for example, in the case of anti-acne compositions. In all embodiments of the present invention, the use is however preferably cosmetic (non-therapeutic).

The cosmetic or pharmaceutical compositions according to the present invention are in particular topically applied to mammalian keratinous tissue such as in particular to human skin or the human scalp and hair.

The term "cosmetic composition" as used in the present application refers to cosmetic compositions as defined under the heading "Kosmetika" in Römpp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), $4^{th}$ edition, 1992.

Suitable surfactants, emulsifiers, thickeners, and oils for the purpose of the present inventions are alls surfactants, emulsifiers, thickeners, and oils commonly used in cosmetic applications and which are e.g. listed in CTFA Cosmetic Ingredient Handbook, First edition 1988. Such suitable surfactants, emulsifiers, thickeners, and oils are well known to a person skilled in the art.

The compositions according to the present invention are generally prepared by admixing erythrulose in an amount selected in the range of 0.005 to 0.75 wt.-%, more preferably in the range of about 0.01 to 0.6 wt.-%, most preferably in the range of about 0.025 to 0.5 wt.-% such as in the range of 0.04 to 0.5 wt.-% based on the total weight of the composition with a suitable carrier. Other suitable ranges include 0.04 to 0.2 wt.-% and 0.05 to 0.1 wt.-%. Further particular ranges include 0.01 to 0.2 wt.-% or 0.05 to 0.2 wt.-%, respectively 0.01 to 0.15 or 0.05 to 0.15 wt.-%.

The cosmetic or pharmaceutical compositions according to the present invention preferably further comprise a physiologically acceptable medium, that is to say a medium compatible with keratinous substances, such as the skin, mucosa, and keratinous fibres. In particular the physiologically acceptable medium is a cosmetically or pharmaceutically acceptable carrier.

The term cosmetically or pharmaceutically acceptable carrier refers to all carriers and/or excipients and/or diluents conventionally used in cosmetic compositions or pharmaceutical compositions.

Preferably, the cosmetic or pharmaceutical compositions according to the invention are in the form of a suspension or dispersion in solvents or fatty substances, or alternatively in the form of an emulsion or micro emulsion (in particular of O/W- or W/O-type), PIT-emulsion, nano emulsion, multiple emulsion (e. g. O/W/O- or W/O/W-type), pickering emulsion, hydrogel, lipogel, one- or multiphase solution or vesicular dispersion.

The cosmetic or pharmaceutical compositions in accordance with the invention can be in the form of a liquid, lotion, a thickened lotion, a gel, a cream, a milk, an ointment or a paste.

The cosmetic or pharmaceutical compositions according to the invention have a pH in the range of 3-10, preferably in the range of pH of 3-8, most preferred in the range of pH 3.5-6.5. The pH is adjusted by methods known to a person skilled in the art, e.g. by using an acid such as a hydroxy acid including glycolic acid, lactic acid, malic acid, citric acid and tartaric acid or a base such as e.g. sodium or potassium hydroxide or ammonium hydroxide as well as mixtures thereof.

Preferably, in the compositions according to the invention citric acid is used in an amount of at least 0.0001 wt.-%, such as e.g. in an amount of 0.01-1 wt.-%, in particular in an amount of 0.01 to 0.5 wt.-% is used for pH adjustment.

The cosmetic compositions according to the present invention are in particular skin care preparations, functional preparations and/or hair care preparations such as most in particularly skin or hair care preparations.

Examples of skin care preparations are, in particular, light protective preparations, anti-ageing preparations, preparations for the treatment of photo-ageing, body oils, body lotions, body gels, treatment creams, skin protection ointments, moisturizing preparations such as moisturizing gels or moisturizing sprays, face and/or body moisturizers, as well as skin lightening preparations.

Preferably in all embodiments of the present invention the skin care preparation is a deodorant, an anti-perspirant, or an anti-acne composition.

Examples of functional preparations are cosmetic compositions containing active ingredients such as hormone preparations, vitamin preparations, vegetable extract preparations, anti-ageing preparations, and/or antimicrobial (antibacterial or antifungal) preparations without being limited thereto.

Examples of hair care preparations which are suitable according to the invention and which may be mentioned are shampoos, hair conditioners (also referred to as hair rinses), hairdressing compositions, hair tonics, hair regenerating compositions, hair lotions, water wave lotions, hair sprays, hair creams, hair gels, hair oils, hair pomades or hair brilliantines. Accordingly, these are always preparations which are applied to the hair and the scalp for a shorter or longer time depending on the actual purpose for which they are used.

If the hair care preparations according to the invention are supplied as shampoos, these can be clear liquids, opaque liquids (with pearly luster effect), in cream form, gel-like or else in powder form or in tablet form, and as aerosols. The surfactant raw materials on which these shampoos are based can be anionic, cationic, nonionic and amphoteric in nature and also be present in combinations of these substances.

Examples of anionic surfactants suitable for the incorporation into the shampoo preparations according to the present invention are $C_{10-20}$ alkyl- and alkylenecarboxylates, alkyl ether carboxylates, fatty alcohol sulfates, fatty alcohol ether sulfates, alkylolamide sulfates and sulfonates, fatty acid alkylolamide polyglycol ether sulfates, alkanesulfonates and hydroxyalkanesulfonates, olefinsulfonates, acyl esters of isothionates, alpha-sulfo fatty acid esters, alkylbenzenesulfonates, alkylphenol glycol ether sulfonates, sulfosuccinates, sulfosuccinic monoesters and diesters, fatty alcohol ether phosphates, protein-fatty acid condensation products, alkyl monoglyceride sulfates and sulfonates, alkyl glyceride ether sulfonates, fatty acid methyltaurides, fatty acid sarcosinates, and sulforicinoleates. These compounds and their mixtures are used in the form of their salts which are soluble in water or dispersible in water, for example the sodium, potassium, magnesium, ammonium, mono-, di- and triethanolammonium and analogous alkylammonium salts.

Examples of suitable cationic surfactants are quaternary ammonium salts such as di($C_{10}$-$C_{24}$alkyl)dimethylammonium chloride or bromide, preferably di ($C_{12}$-$C_{18}$alkyl)-dimethylammonium chloride or bromide; $C_{10}$-$C_{24}$-alkyldimethylethylammonium chloride or bromide; $C_{10}$-$C_{24}$-alkyltrimethylammonium chloride or bromide, preferably cetyltrimethylammonium chloride or bromide and $C_{20}$-$C_{24}$-alkyltrimethylammonium chloride or bromide; $C_{10}$-$C_{24}$-alkyldimethylbenzylammonium chloride or bromide, preferably $C_{12}$-$C_{18}$-alkyldimethylbenzylammoniumchloride; N—($C_{12}$-$C_{18}$-alkyl)pyridinium chloride or bromide, preferably N—($C_{12}$-$C_{16}$-alkyl)pyridinium chloride or bromide; N—($C_{12}$-$C_{18}$-alkyl)isoquinolinium chloride, bromide or monoalkyl sulfate; N—($C_{12}$-$C_{18}$-alkyloylcolaminoformylmethyl)pyridinium chloride; N—($C_{12}$-$C_{18}$-alkyl)-N-methylmorpholinium chloride, bromide or monoalkyl sulfate; N—($C_{12}$-$C_{18}$-alkyl)-N-ethylmorpholinium chloride, bromide or monoalkyl sulfate; $C_{16}$-$C_{18}$-alkylpentaoxethylammonium chloride; isobutylphenoxyethoxyethyldimethyl-benzylammonium chloride; salts of N,N-diethylaminoethylstearylamide and oleylamide with hydrochloric acid, acetic acid, lactic acid, citric acid, phosphoric acid; N-acylamidoethyl-N,N-diethyl-N-methylammonium chloride, bromide or monoalkylsulfate and N-acylaminoethyl-N,N-diethyl-N-benzylammonium chloride, bromide or monoalkyl sulfate, where acyl is preferably stearyl or oleyl.

Examples of suitable nonionic surfactants which can be used as detergent substances are fatty alcohol ethoxylates (alkylpolyethylene glycols); alkylphenol polyethylene glycols; alkyl mercaptan polyethylene glycols; fattyamine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); sucrose esters; sorbitol esters and polyglycol ether.

Examples of amphoteric surfactants which can be added to the shampoos are N—($C_{12}$-$C_{18}$-alkyl)-.beta.-aminopropionates and N—($C_{12}$-$C_{18}$-alkyl)-.beta.-iminodipropionates as alkali metal and mono-, di- and trialkylammonium salts; N-acylamidoalkyl-N,N-dimethylacetobetaine, preferably N—($C_8$-$C_{18}$-acyl)amidopropyl-N, N-dimethylacetobetaine; $C_{12}$-$C_{18}$-alkyldimethylsulfopropylbetaine; amphoteric surfactants based on imidazoline (commercial name: Miranol®, Steinapon®), preferably the sodium salt of 1-(β-carboxymethyloxyethyl)-1-(carboxymethyl)-2-laurylimidazolinium; amine oxide, for example $C_{12}$-$C_{18}$-alkyldimethylamine oxide, fatty acid amidoalkyldimethylamine oxide.

The hair care preparations according to the invention can additionally contain further additives customary in hair care such as for example perfumes, colorants, also those which simultaneously dye or tint the hair, solvents, opacifying agents and pearly luster agents, for example esters of fatty acids with polyols, magnesium and zinc salts of fatty acids, dispersions based on copolymers, thickening agents such as sodium, potassium and ammonium chloride, sodium sulfate, fatty acid alkylolamides, cellulose derivatives, natural rubbers, also plant extracts, protein derivatives such as gelatin, collagen hydrolysates, polypeptides with a natural or synthetic basis, egg yolk, lecithin, lanolin and lanolin derivatives, fats, oils, fatty alcohols, silicones, deodorizing agents, substances with antimicrobial activity, substances with anti-seborrhoeic activity, substances with keratolytic and keratoplastic effect, such as, for example, sulfur, salicylic acid and enzymes as well as further anti-dandruff agents such as olamine, climbazol, zinc pyrithion, ketoconazole, salicylic acid, sulfur, tar preparations, derivatives of undecenic acid, extracts of nettel, rosemary, cottonwood, birch, walnut, willow bark and/or arnica.

For the preparation of the hair care preparations the erythrulose is dissolved under stirring at a temperature in the range between 20 and 40° C., preferably at room temperature. Subsequently, the further additives are added.

In the event of alcohol containing scalp respectively hair care preparations erythrulose is dissolved in the alcohol at a temperature in the range between 20 and 40° C., preferably at room temperature. Subsequently, the further additives are added. In the event of hair rinses and oil-in-water emulsions the active substance is added to the final emulsion below 40° C. under stirring.

The shampoos are produced in a manner known per se by mixing the individual components and where necessary further processing appropriate for the particular type of preparation.

Examples of hair care preparations in which the erythrulose can be used according to the invention and which may be mentioned are hair conditioners, hair tonics and hair regenerating compositions, which are rinsed off from the hair after a certain time or, depending on the formulation, can also remain on the hair. These products contain, inter alia, substances from the group of the above mentioned cationic substances which display a reviving and antistatic property on the hair.

All these preparations are also produced as already mentioned for the shampoo in a manner known per se with the addition of the erythrulose.

Particular suitable hair care preparations according to the present invention are shampoo preparations comprising (i) erythrulose in an amount selected in the range of 0.005 to 0.75 wt.-%, more preferably in the range of about 0.01 to 0.6 wt.-%, most preferably in the range of about 0.025 to 0.5 wt.-% such as in the range of 0.04 to 0.5 wt.-%, based on the total weight of the composition, (ii) water and (iii) at least one anionic surfactant. Preferably, the anionic surfactant is selected from the group consisting of sodium lauryl sulfate, ammonium lauryl sulfate, sodium lauryl ether sulfate, ammonium lauryl ether sulfate, sodium lauroyl sarconisate, sodium oleylsuccinate, ammonium lauryl sulfosuccinate, sodium dodecylbenzol sulfonate and/or triethanolamine dodecylbenzol sulfonate or mixtures thereof, such as in particular sodium lauryl sulfate, ammonium lauryl sulfate, sodium lauryl ether sulfate and/or ammonium lauryl ether sulfate. The total amount of the anionic surfactant in the compositions according to the invention ranges from 0.5 to 45 wt.-%, preferably from 1.5 to 35 wt.-%, more preferably from 7 to 25 wt.-%, in particular from 7 to 15 wt.-% based on the total weight of the composition.

Particular suitable hair conditioners according to the present invention may be rinse off or leave on conditioners, preferably rinse-off conditioners. Particular advantageous hair conditioners according to the present invention comprise (i) erythrulose in an amount selected in the range of 0.005 to 0.75 wt.-%, more preferably in the range of about 0.01 to 0.6 wt.-%, most preferably in the range of about 0.025 to 0.5 wt.-% such as in the range of 0.04 to 0.5 wt.-%, most preferably in the range of 0.05 to 0.5 wt.-%, based on the total weight of the composition, (ii) water and (iii) at least one conditioning agent such as e.g. silicone oils, quaternary polymers, naturally derived conditioning agents, etc.

The quaternary polymer is preferably selected from e.g. Polyquaternium-6 (e.g. commercialized under the trade name TILAMAR® Quat 640 or 641), Polyquaternium-22 (e.g. commercialized under the trade name TILAMAR® Quat 2240 or 2241), Polyquaternium-7 (e.g. commercialized under the trade name TILAMAR® Quat 710, 711 or 712), etc. The naturally derived conditioning agents are preferably selected from e.g. sugar based polymers such as Guar Hydroxypropyltrimonium Chloride (e.g. commercialized under the trade name Jaguar C-17, Jaguar C-1000, Jaguar C-13S), but not limited hereto.

In principal any silicone oil is suitable for use in the hair conditioner. However, the silicone oil is preferably selected from dimethicones, dimethiconols, polydimethylsiloxanes, arylated silicones, cyclic silicones, silicone surfactants and aminated silicones and may be volatile or non volatile. Particular suitable silicone oils are dimethicone, dimethiconol, polydimethylsiloxane which are available from various suppliers such as Dow Corning. The total amount of the at least one silicone oil and/or quaternary polymer and/or naturally derived conditioning agent in the hair conditioner is preferably selected is in the range of 0.01 to 10 wt.-%, preferably 0.02 to 7.5 wt.-%, more preferably 0.05 to 5 wt.-% and most preferably 0.1 to 3 wt.-%, based on the total weight of the composition.

In another preferred embodiment, the cosmetic compositions according to the present invention are O/W emulsions, W/O emulsions and/or gels such as shower gels or hair gels.

The O/W emulsions according to the present invention advantageously comprise (i) erythrulose in an amount selected in the range of 0.005 to 0.75 wt. %, more preferably in the range of about 0.01 to 0.6 wt.-%, most preferably in the range of about 0.025 to 0.5 wt.-% such as in the range of 0.04 to 0.5 wt.-%, based on the total weight of the composition, (ii) water and (iii) at least one O/W- or Si/W-emulsifier selected from the list of glycerylstearatcitrate, glycerylstearate (self emulsifying), stearic acid, salts of stearic acid, polyglyceryl-3-methylglycosedistearate, ceteareth-20, steareth-2, steareth-12, PEG-40 stearate, phosphate esters and the salts thereof such as cetyl phosphate (Amphisol® A), diethanolamine cetyl phosphate (Amphisol® DEA), potassium cetyl phosphate (Amphisol® K), sodiumcetearylsulfat, sodium glyceryl oleate phosphate, hydrogenated vegetable glycerides phosphate, sorbitan oleate, sorbitan sesquioleate, sorbitan isostearate, sorbitan trioleate, lauryl glucoside, decyl glucoside, sodium stearoyl glutamate, sucrose polystearate and Hydrated Polyisobuten as well as mixtures thereof. Also, one or more synthetic polymers may be used as an emulsifier such as for example, PVP eicosene copolymer, acrylates/C10-3o alkyl acrylate crosspolymer, acrylates/steareth-20 methacrylate copolymer, PEG-22/dodecyl glycol copolymer, PEG-45/dodecyl glycol copolymer, and mixtures thereof. In a particular preferred embodiment the O/W-emulsifier is selected from the group of cetyl phosphates such as in particular potassium cetyl phosphate (commercially available as Amphisol® K), glyceryl stearate (and) PEG-100 stearate (commercially available as Arlacel® 165) and/or polyalkylenglycolether such as in particular laureth-35 (lauryl alcohol with 35 EO units; commercially available as Brij® 35). The at least one O/W emulsifier is preferably used in an amount of about 0.001 to 10 wt.-%, more preferably in an amount of 0.1 to 7 wt.-% with respect to the total weigh of the composition. Additionally, the cosmetic composition in the form of a O/W emulsion contains advantageously at least one co-emulsifier selected from the list of alkyl alcohols such as Cetyl Alcohol (Lorol C16, Lanette 16) Cetearyl Alcohol (Lanette® O), Stearyl Alcohol (Lanette® 18), Behenyl Alcohol (Lanette® 22), Glyceryl Monostearate, Glyceryl Myristate (Estol® 3650), Hydrogenated Coco-Glycerides (Lipocire Na10) without being limited to this and mixtures thereof.

The W/O emulsions according to the present invention advantageously comprise (i) erythrulose in an amount selected in the range of 0.005 to 0.75 wt.-%, more preferably in the range of about 0.01 to 0.6 wt.-%, most preferably in the range of about 0.025 to 0.5 wt.-% such as in the range of 0.04 to 0.5 wt.-%, based on the total weight of the composition, (ii) water and (iii) at least one W/O- or W/Si-emulsifier selected from the list of polyglyceryl-2-dipolyhydroxystearat, PEG-30 dipolyhydroxystearat, cetyl dimethicone copolyol, polyglyceryl-3 diisostearate polyglycerol esters of oleic/isostearic acid, polyglyceryl-6 hexaricinolate, polyglyceryl-4-oleate, polygylceryl-4 oleate/PEG-8 propylene glycol cocoate, magnesium stearate, sodium stearate, potassium laurate, potassium ricinoleate, sodium cocoate, sodium tallowate, potassium castorate, sodium oleate, and mixtures thereof. Further suitable W/Si-emulsifiers are Lauryl Polyglyceryl-3 Polydimethylsiloxyethyl Dimethicone and/or PEG-9 Polydimethylsiloxyethyl Dimethicone and/or Cetyl PEG/PPG-10/1 Dimethicone and/or PEG-12 Dimethicone Crosspolymer and/or PEG/PPG-18/18 Dimethicone. The at least one W/O emulsifier is preferably used in an amount of about 0.001 to 10 wt.-%, more preferably in an amount of 0.2 to 7 wt.-% with respect to the total weigh of the composition.

The gel preparations according to the present invention advantageously comprise (i) erythrulose in an amount selected in the range of 0. 0.005 to 0.75 wt.-%, more preferably in the range of about 0.01 to 0.6 wt.-%, most preferably in the range of about 0.025 to 0.5 wt.-% such as in the range of 0.04 to 0.5 wt.-%, most preferably in the range of 0.05 to 0.5 wt.-%, based on the total weight of the composition, (ii) water and (iii) at least one water soluble thickener. Such water-soluble thickeners are well known to a person skilled in the art and are e.g. listed in the "Handbook of Water soluble gums and resins" by Robert L. Davidson (Mc Graw Hill Book Company (1980)). Particularly suitable water soluble thickeners are selected from the group consisting of polyacrylic acids (e.g. commercially available under the tradename Carbomer or Carbopol®), homopolymers of 2-Acrylamido-2-methylpropansulfonic acid (e.g. commercially available as Rheothik®11-80), acrylate copolymers (e.g. commercially available under the tradename Pemulen® or Aculyn® 33), branched Poly(methacryloyloxyethyltrimethylammoniumchlorid) (INCI-name Polyquaternium-37), non-modified guar gums (e.g. commercially available under the tradename Jaguar), starch or derivatives thereof and/or hydroxyalkylcellulosen. Preferably the water-soluble thickener is used in an amount of about 0.001 to 10 wt.-%, more preferably in an amount of 0.1 wt.-% to 7 wt.-%, based on the total weigh of the composition.

The following examples are provided to further illustrate the compositions and effects of the present invention. These examples are illustrative only and are not intended to limit the scope of the invention in any way.

EXAMPLE 1: ANTIMICROBIAL EFFICACY

The antimicrobial efficacy is assessed in analogy to the regulatory challenge test method (NF EN ISO11930). Thus, a solution of Erythrulose from DSM Nutritional products in two different concentrations was prepared under sterile conditions. For this the Erythrulose was solubilized in physiological serum with 0.85 wt.-% NaCl. Phenoxyethanol was solubilized in a physiological serum with 0.85 wt.-% NaCl further comprising 5 wt.-% ethanol to ensure solubility. The solutions were deposed in 96-deep well plates (1.6 ml/well). The wells were contaminated with the respective bacterial or the fungal strains at $1.9*10^5$ to $8.1*10^5$ cfu/ml for the bacteria and $3.3*10^3$ to $3.8*10^4$ cfu/ml for the fungi to obtain the initial contamination as outlined in table 1 and 2. After contamination each well was thoroughly mixed to ensure a homogeneous distribution of the microorganism. Then each plate was incubated at 22° C. for 24 h. The counting of the (remaining) population was carried out 24 h after contamination.

TABLE 1

Erythrulose, 0.4% active

| Bacteria/fungi | Erythrulose (0.4 wt.-%) colony counts [cfu/ml] | | Phenoxyethanol (0.5 wt.-%) colony counts [cfu/ml] | |
|---|---|---|---|---|
| | 0 h | 24 h | 0 h | 24 h |
| P. Acnes (acne, gram+) | 500000 | 55000 | 500000 | 260000 |
| S. epidermidis (deo, gram+) | 500000 | 0 | 500000 | 3300 |
| C. xerosis (deo, gram+) | 810000 | 0 | 810000 | 0 |
| A. brasiliensis (preserv., mold) | 38000 | 330 | 38000 | 78 |
| C. albicans (preserv., yeast) | 19000 | 78 | 19000 | 1000 |
| P. aeruginosa (preserv., gram−) | 810000 | 0 | 810000 | 280000 |
| E. coli (preserv., gram−) | 440000 | 280000 | 440000 | 530000 |
| S. aureus (preserv., gram+) | 190000 | 0 | 190000 | 78000 |

TABLE 2

Erythrulose, 0.08% active

| | t0 | 24 h |
|---|---|---|
| Propionibacterium acnes (acne, gram+) | 310000 | 3300 |
| Staphylococcus epidermidis (deo, gram+) | 560000 | 0 |
| Corynebacterium xerosis (deo, gram+) | 250000 | 55 |
| Aspergillus brasiliensis (preserv., mold) | 10000 | 10 |
| Pseudomonas aeruginosa (preserv., gram−) | 450000 | 530000 |
| Escherichia coli (preserv., gram−) | 250000 | 530000 |

As can be retrieved from table 1 erythrulose exhibits an equal or even better activity against microbes as the preservative phenoxyethanol, a well-known preservative in cosmetics, even at lower concentrations (0.4 wt.-% vs 0.5 wt. %).

Furthermore, the results in table 2 illustrate that Erythrulose is particularly and selectively active against microbial cells responsible for the odor formation from sweat e.g. in the axilla, i.e. S. epidermidis and C. xerosis even at very low concentrations, which makes it particularly suitable for deodorant applications while at this concentration level it is not active anymore against other microbes such as P. aeruginosa and E. coli.

The results in table 2 furthermore illustrate that erythrulose at very low concentration still excerpts a good antimicrobial activity against P. acnes, making it suitable for a mild anti-acne treatment.

Furthermore, it also suitable at such low concentration levels to protect products from microbial decay caused by A. brasiliensis.

EXAMPLE 2: O/W FOUNDATION

| Ingredients | INCI | wt. % |
| --- | --- | --- |
| Deionised Water | Aqua | Ad 100 |
| Glycerin | Glycerin | 2.00 |
| Triethanolamine | Triethanolamine | 0.80 |
| Paratexin M | Methylparaben EP | 0.20 |
| Keltrol | Xanthan Gum | 0.30 |
| Erythrulose | Erythrulose | 0.10 |
| Titanium dioxide | C.I. 77891 | 4.57 |
| SunCROMA yellow iron oxide | C.I. 77492 | 0.30 |
| SunCROMA red iron oxide | C.I. 77491 | 0.13 |
| SunCROMA black iron oxide | C.I. 77499 | 0.20 |
| DC 556 | Phenyl Trimethicone | 3.60 |
| Stearic Acid | Stearic Acid | 1.4 |
| Cetyl Alcohol | Cetyl Alcohol | 3.0 |
| Paratexin P | Propylparaben EP | 0.1 |

EXAMPLE 3: ALCOHOL FREE FACIAL TONIC

| Ingredients | INCI | wt. % |
| --- | --- | --- |
| Polysorbate-20 | Polysorbate-20 | 2.00 |
| ALPAFLOR CALENDULA AO | Calendula Officinalis Extract, Glycerin, Water | 0.80 |
| ALPAFLOR BUDDLEJA AO | Buddleja Davidii Extract, Glycerin, Water | 0.80 |
| Arlasilk Phospholipd CDM | Sodium Coco PG-Dimonium Chloride Phosphate | 0.50 |
| Fragrance | Parfum | 0.10 |
| Deionised Water | Aqua | Ad 100 |
| Citric Acid | Citric Acid | 0.01 |
| Erythrulose | Erythrulose | 0.75 |
| Paratexin FRP | Ethylparaben, Butylparaben, Propylparaben, Isobutylparaben | 0.10 |

EXAMPLE 4: W/O CREAM

| Ingredients | INCI | wt. % |
| --- | --- | --- |
| Cremophor WO-7 | PEG-7 Hydrogenated Castor Oil | 2.50 |
| Elfacos ST-9 | PEG-45/Dodecyl Glycol Copolymer | 2.00 |
| Cirebelle 303 | Synthetic Wax | 5.00 |
| Cirebelle 109L | Synthetic Wax | 7.20 |
| Miglyol 818 | Caprylic/Capric/Linoleic Triglyceride | 5.00 |
| Eutanol G | Octyldodecanol | 7.50 |
| Cetiol OE | Dicaprylyl Ether | 9.20 |
| Deionised Water | Aqua | Ad 100 |
| Glycerin | Glycerin | 5.00 |
| Propylene Glycol | Propylene Glycol | 2.00 |
| Euxyl PE 9010 | Phenoxyethanol and Ethylhexylglycerin | 0.80 |
| Erythrulose | Erythrulose | 0.1 |

EXAMPLE 5: SOOTHING GEL

| Ingredients | INCI | wt. % |
| --- | --- | --- |
| Deionised Water | Aqua | Ad 100 |
| Keltrol CG RD | Xanthan Gum | 0.50 |
| Sodium Benzoate | Sodium Benzoate | 0.20 |
| Potassium Sorbate | Potassium Sorbate | 0.25 |
| ALPAFLOR MARRABIUM AO | Glycerin, Aqua, Marrubium Vulgare, Sodium Benzoate, Potassium Sorbate | 3.00 |
| Erythrulose | Erythrulose | 0.40 |

EXAMPLE 6: O/W LOTION

| Ingredients | INCI | wt. % |
| --- | --- | --- |
| Deionised Water | Aqua | Ad 100 |
| Menthol | Menthol | 0.10 |
| Keltrol CG SFT | Xanthan Gum | 1.25 |
| Ceralution ES | Ceteareth-25, Di Sodium Ethylene Dicocamide PEG-15 Disulfate | 2.00 |
| Isofol 20 | Octyldodecanol | 5.00 |
| Paratexin EC5 | Benzoic Acid Benzyl Alcohol, Dehydoacetic Acid, Sorbic Acid | 1.00 |
| Erythrulose | Erythrulose | 0.25 |

EXAMPLE 7: FACIAL CLEANSING GEL

| Ingredients | INCI | wt. % |
| --- | --- | --- |
| Deionised Water | Aqua | Ad 100 |
| Carbopol AQUA SF-1 Polymer | Acrylates Copolymer | 7.50 |
| Texapon NSO-BZ | Sodium Laureth Sulfate | 41.00 |
| Miranol Ultra C 32 | Sodium Cocoamphoacetate | 5.00 |
| Hostapon CLG | Sodium Lauroyl Glutamate | 4.50 |
| Jaguar C162 | Hydroxypropyl Guar Hydroxypropyltrimonium Chloride | 1.00 |
| Erythrulose | Erythrulose | 0.50 |
| Euxyl K 300 | Phenoxyethanol & Methylparaben & Propylparaben & Ethylparaben & Butylparaben & Isobutylparaben | 0.80 |
| ALPAFLOR MALVA AO | Glycerin, Aqua, Malva Sylvestris (Mallow) Flower Extract, Potassium Sorbate, Sodium Benzoate | 2.00 |
| Parfum Limette | Fragrance | q.s. |
| FD&C Yellow 5 | CI 19140 | 0.50 |
| Frescolat Plus | Menthyl Lactate, Menthol | 0.20 |
| Dehyton AB-30 | Coco Betaine | 2.00 |
| Rewoderm LI S 80 | PEG-200 Hydrogenated Glyceryl Palmate & PEG-7 Glyceryl Cocoate | 1.00 |
| Citric Acid | Citric Acid | q.s. |

EXAMPLE 8: LEAVE-ON HAIR AND SCALP CONDITIONER

| Ingredients | INCI | wt. % |
| --- | --- | --- |
| Deionised Water | Aqua | Ad 100 |
| Ethanol DEB 96 | Alcohol denat. | 30.00 |
| PVP/VA Copolymer | PVP/VA Copolymer | 2.50 |
| Euxyl K-300 | Phenoxyethanol, Methylparaben, Butylparaben, Ethylparaben, Propylparaben, Isobutylparaben | 0.80 |
| Protachem HCO-40 | PEG-40 Hydrogenated Castor Oil | 0.50 |
| Fragrance ADAM | Parfum | 0.10 |
| Triethanolamine 99% | Triethanolamine | 0.01 |
| FD & C Yellow No 5 (0.5% Solution) | CI 19140, Aqua | 0.10 |
| FD & C Blue No 1 (0.5% Solution) | CI 42090, Aqua | 0.10 |
| Erythrulose | Erythrulose | 0.05 |

EXAMPLE 9: SHAMPOO

| INCI Nomenclature | wt. % |
|---|---|
| Aqua (water) | Ad 100 |
| Ammonium laureth sulfate | 10.00 |
| Ammonium lauryl sulfate | 5.00 |
| Glycol distearate | 1.00 |
| Dimethicone | 1.00 |
| Cetyl alcohol | 0.50 |
| Cocamide MEA | 3.00 |
| Erythrulose | 0.30 |
| ZPT | 0.50 |
| Guar hydroxypropyltrimonium chloride | 0.20 |
| Hydrogenated polydecene | 1.00 |
| Polyquaternium 10 | 0.30 |
| PEG 7m | 0.50 |
| Trimethylpropane tricaprylate/tricaprate | 1.00 |
| Preservative | q.s. |
| Fragrance | 0.30 |
| E 104, E 110, E 132 | 0.02 |

EXAMPLE 10: CLEAR SHAMPOO WITH PLANT EXTRACTS

| INCI Nomenclature | wt. % |
|---|---|
| Aqua (water) | Ad 100 |
| Sodium laureth sulfate | 10.00 |
| Lauryl glucoside | 6.00 |
| Cocamidopropyl betaine, | 2.00 |
| Propylene glycol | 2.00 |
| Perfume oil | 1.25 |
| Sodium citrate | 0.25 |
| Sodium benzoate | 0.20 |
| Panthenol | 1.00 |
| Sodium formate | 0.20 |
| Polyquaternium-10 | 0.20 |
| Hydroxypropyl guar hydroxypropyltrimonium chloride | 0.05 |
| Erythrulose | 0.25 |
| PEG-35 castor oil | 1.00 |
| Maris sal | 1.25 |
| Polysorbate 20 | 1.00 |
| Tocopheryl acetate | 0.20 |
| *Prunus armeniaca* | 0.20 |
| *Echinacea purpurea* | 0.05 |
| Tocopherol | 0.05 |
| Linoleic acid | 0.20 |
| Preservative | 1.00 |
| CI77891 | 0.02 |

EXAMPLE 11: RINSE-OFF HAIR AND SCALP CONDITIONER

| INCI Nomenclature | wt. % |
|---|---|
| Aqua (water) | Ad 100 |
| Stearyl alcohol | 2.50 |
| Cetyl alcohol | 2.50 |
| Behentrimonium chloride | 1.30 |
| Dimethicone | 2.00 |
| Erythrulose | 0.50 |
| Fragrance | 0.50 |
| Butylene glycol | 2.00 |
| Methyl parabene | 0.30 |

The invention claimed is:

1. A method of inhibiting microbial growth of microbes selected from the group consisting of *Propionibacterium acnes* (*P. acnes*), *Staphylococcus epidermis* (*S. epidermis*), *Cornyebacterium xerosis* (*C. xerosis*), *Aspergillus brasiliensis* (*A. brasiliensis*) and mixtures thereof in a product composition, wherein the method comprises incorporating into the product composition in need of microbial inhibition an antimicrobial growth inhibiting amount of erythrulose.

2. The method according to claim 1, wherein the product composition is selected from the group consisting of cosmetic compositions, household product compositions, plastic product compositions, paper product compositions and paint product compositions.

3. The method according to claim 2, wherein the method improves preservation of the product composition against microbial decay and breakdown as compared to a product composition not containing the erythrulose.

4. The method according to claim 1, wherein the erythrulose is incorporated into the product composition as a deodorant active compound.

5. The method according to claim 1, wherein the erythrulose is incorporated into a cosmetic product composition as an anti-acne compound.

6. The method according to claim 1, wherein the method prevents the microbial decay and breakdown caused by *A. brasiliensis* of the product composition, and wherein the method comprises adding to the product composition an effective antimicrobial decay and breakdown preventing amount in a range of 0.005 to 0.75 wt. %, based on the total weight of the product composition, of the erythrulose.

7. The method according to claim 6, wherein the effective antimicrobial decay and breakdown preventing amount of the erythrulose is 0.01 to 0.6 wt. %, based on the total weight of the product composition.

8. The method according to claim 6, wherein the product composition further comprises water and at least one agent selected from the group consisting of surfactants, emulsifiers, thickeners and oils.

9. The method according to claim 6, wherein the product composition is a cosmetic composition in a form of a shampoo preparation, a hair conditioner, an oil-in-water (O/W) emulsion, a water-in-oil (W/O) emulsion or a gel.

10. The method according to claim 6, wherein the effective antimicrobial decay and breakdown preventing amount of the erythrulose is 0.025 to 0.5 wt. %, based on the total weight of the product composition.

11. The method according to claim 6, wherein the effective antimicrobial decay and breakdown preventing amount of the erythrulose is 0.04 to 0.05 wt. %, based on the total weight of the product composition.

* * * * *